US011179080B2

(12) United States Patent
Duval et al.

(10) Patent No.: US 11,179,080 B2
(45) Date of Patent: Nov. 23, 2021

(54) SYSTEMS AND METHODS FOR RAPID CALIBRATION OF OPTICAL MEDICAL SENSORS

(71) Applicant: Boston Scientific Scimed, Inc., Maple Grove, MN (US)

(72) Inventors: George Wilfred Duval, Sudbury, MA (US); Gang Hu, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 345 days.

(21) Appl. No.: 16/041,915

(22) Filed: Jul. 23, 2018

(65) Prior Publication Data

US 2019/0021637 A1   Jan. 24, 2019

Related U.S. Application Data

(60) Provisional application No. 62/536,140, filed on Jul. 24, 2017.

(51) Int. Cl.
*A61B 5/1455* (2006.01)
*A61B 5/1495* (2006.01)
(Continued)

(52) U.S. Cl.
CPC .......... *A61B 5/1495* (2013.01); *A61B 5/0084* (2013.01); *A61B 5/02255* (2013.01);
(Continued)

(58) Field of Classification Search
None
See application file for complete search history.

(56) References Cited

U.S. PATENT DOCUMENTS

| 6,018,673 A | 1/2000 | Chin et al. |
| 2012/0209086 A1 | 8/2012 | Beute |

(Continued)

FOREIGN PATENT DOCUMENTS

| WO | 2013166465 | 11/2013 |
| WO | 2016086053 | 6/2016 |

OTHER PUBLICATIONS

"Afe4405 Ultra-Small, Integrated AFE with FIFO for Wearable, Optical Heart-Rate Monitoring and Bio-Sensing," Texas Instruments Datasheet, Revised May 2016 (11 pages).

(Continued)

*Primary Examiner* — Eric F Winakur
*Assistant Examiner* — Marjan Fardanesh
(74) *Attorney, Agent, or Firm* — Pauly, DeVries Smith & Deffner LLC (57) ABSTRACT

Embodiments herein relate to systems and methods for rapidly calibrating optical medical sensors. In an embodiment, a method can include placing a reflective optical medical sensor device on or in a patient. The reflective optical medical sensor device can include one or more optical emitters; one or more optical detectors; and a measurement circuit having one or more transimpedance amplifiers (TIA). The method can include setting the TIA to a fixed gain value and then turning on the optical emitter associated with each spatially unique measurement vector and receiving reflected light with the associated optical detector for each spatially unique measurement vector at the same fixed gain value. The method can include assessing the signal-to-noise (SNR) for each spatially unique measurement vector and selecting the spatially unique measurement vector having the highest SNR. Other embodiments are also included herein.

20 Claims, 6 Drawing Sheets

(51) Int. Cl.
    *A61B 5/00*     (2006.01)
    *A61B 5/0225*     (2006.01)
    *A61B 5/024*     (2006.01)

(52) U.S. Cl.
    CPC ...... *A61B 5/02427* (2013.01); *A61B 5/14551* (2013.01); *A61B 5/7221* (2013.01); *A61B 5/7225* (2013.01); *A61B 5/6852* (2013.01); *A61B 5/7203* (2013.01)

(56) References Cited

U.S. PATENT DOCUMENTS

| | | | |
|---|---|---|---|
| 2013/0041268 | A1 | 2/2013 | Rimoldi et al. |
| 2013/0324816 | A1 | 12/2013 | Bechtel et al. |
| 2014/0012144 | A1 | 1/2014 | Crone et al. |
| 2014/0243632 | A1 | 8/2014 | Ulrich et al. |
| 2015/0374245 | A1 | 12/2015 | Szilagyi |
| 2016/0120444 | A1* | 5/2016 | Hsu ................ G01J 3/0272 600/476 |
| 2017/0055907 | A1* | 3/2017 | Altebaeumer ..... A61B 5/02416 |
| 2017/0127959 | A1 | 5/2017 | Paulussen et al. |
| 2018/0020960 | A1 | 1/2018 | Sarussi et al. |
| 2018/0353075 | A1 | 12/2018 | Duval |

OTHER PUBLICATIONS

Alzahrani, Abdullah et al., "A Multi-Channel Opto-Electronic Sensor to Accurately Monitor Heart Rate against Motion Artifacts during exercise," Sensors 2015, 15, 25681-25702 (22 pages).
"Bpw 34 SR Version 1.3," Datasheet by OSRAM Opto Semiconductors, Mar. 31, 2016 (13 pages).
Chreiteh, Shadi S. et al., "A Clinical Study of Short-Term Sternal Photoplethysmography: Recordings from Patients with Obstructive Airways Diseases," 2016 38th Annual International Conference of the IEEE Engineering in Medicine and Biology Society (EMBC), 2016, pp. 2712-2716.
Chreiteh, Shadi S. et al., "Long-Term Quasi-Continuous Oxygen Saturation Levels Obtained from Sternal Photoplethysmography on Patients with Obstructive Lung Diseases," 2016 38th Annual International Conference of the IEEE Engineering in Medicine and Biology Society (EMBC), 2016, pp. 2725-2728.
Fontaine, Alexandra et al., "Reflectance Based Pulse Oximeter for the Chest and Wrist," Worcester Polytechnic Institute, 2013 (131 pages).
Friedland, Shai et al., "Reflectance Spectrophotometry for the assessment of mucosal perfusion in the gastrointestinal tract," Gastrointest Endoscopy Clin N Am 14(2004) 539-553 (15 pages).
Hashemi, Hooman "Transimpedance Amplifiers (TIA): Choosing the best Amplifier for the Job," Texas Instruments Application Report SNOA942A—Nov. 2015—Revised May 2017 (8 pages).
Mendelson, Y. et al., "Noninvasive Pulse Oximetry Utilizing Skin Relectance Photoplethysmography," IEEE Transactions on Biomedical Engineering (1988): 35, 10, 798-805 (8 pages).
"New Sensor for Fitness Tracking in Smarwatches and Fitness Armbands," Press Release by OSRAM Opto Semiconductors, Nov. 8, 2015 (3 pages).
Scholbach, Thomas et al., "Dynamic Tissue Perfusion Measurement in the Intestinal Wall—Correlation with Ulcerative Colitis," J Med Ultrasound 2010;18(2):62-70 (9 pages).
Schreiner, Collin et al., "Blood Oxygen Level Measurement with a Chest-Based Pulse Oximetry Prototype System," Computing in Cardiology, 2010, pp. 537-540.
"Sfh7060 Version 1.1," BioMon Sensor Datasheet by OSRAM Opto Semiconductors, Apr. 20, 2016 (24 pages).
Final Office Action for U.S. Appl. No. 16/004,661 dated Oct. 2, 2020 (19 pages).
Response to Communication Pursuant to Rules 161(1) and 162 EPC for European Patent Application No. 18737747.8 filed Aug. 3, 2020 (14 pages).
Response to Non-Final Rejection dated Apr. 29, 2020 for U.S. Appl. No. 16/004,661, submitted via EFS-Web on Jul. 29, 2020, 13 pages.
International Search Report and Written Opinion for International Application No. PCT/US2018/036823 dated Aug. 30, 2018 (14 pages).
International Preliminary Report on Patentability for PCT Application No. PCT/US2018/036823 dated Dec. 26, 2019 (10 pages).
Non-Final Office Action for U.S. Appl. No. 16/004,661 dated Apr. 29, 2020 (25 pages).
"Non-Final Office Action," for U.S. Appl. No. 16/004,661 dated May 5, 2021 (21 pages).
"Response to Communication Pursuant to Article 94(3) EPC," for European Patent Application No. 18737747.8 filed Apr. 27, 2021 (11 pages).
"Response to Final Rejection," dated Oct. 2, 2020 for U.S. Appl. No. 16/004,661, submitted via EFS-Web on Apr. 1, 2021, 16 pages.
Communication Pursuant to Article 94(3) EPC for European Patent Application No. 18737747.8 dated Dec. 18, 2020 (5 pages).

* cited by examiner

SYSTEMS AND METHODS FOR RAPID CALIBRATION OF OPTICAL MEDICAL SENSORS

This application claims the benefit of U.S. Provisional Application No. 62/536,140, filed Jul. 24, 2017, the content of which is herein incorporated by reference in its entirety.

FIELD

Embodiments herein relate to systems and methods for rapidly calibrating optical medical sensors.

BACKGROUND

In the process of providing health care, clinicians often make physical observations and run tests to gather data about a patient. After collecting data and analyzing other aspects, such as a given patient's health history, the clinician often forms a diagnosis and then selects a therapy to treat the diagnosed condition.

Useful pieces of data to aid in diagnosis and/or monitoring of a patient can be gathered using reflective optical sensors. Optical sensors can operate by emitting light into a tissue of the body (such as by using an LED) and then using an optical detector in order to detect light reflected back from the tissue. The detected reflected light can then be analyzed to determine various aspects regarding the current state of the patient.

SUMMARY

Embodiments herein relate to systems and methods for rapidly calibrating optical medical sensors.

In a first aspect, a method for determining an optimal spatial vector for a reflective optical medical sensor device is included. The method can include placing a reflective optical medical sensor device on or in a patient. The reflective optical medical sensor device can include; one or more optical emitters; one or more optical detectors; and a measurement circuit having one or more transimpedance amplifiers (TIA). Unique pairs of the optical emitters and the optical detectors can define a plurality of spatially unique measurement vectors. The method can include setting the TIA to a fixed gain value and then turning on the optical emitter associated with each spatially unique measurement vector and receiving reflected light with the associated optical detector for each spatially unique measurement vector at the same fixed gain value. The method can include assessing the signal-to-noise (SNR) for each spatially unique measurement vector. The method can include selecting the spatially unique measurement vector having the highest SNR. The method can include conducting ongoing monitoring of the patient by causing the optical emitter associated with the selected spatially unique measurement vector to emit light and receiving reflected light therefrom with the optical detector associated with the selected spatially unique measurement vector.

In a second aspect, in addition to or in place of other aspects herein, the method can further include putting all optical emitters associated with non-selected spatially unique measurement vectors in a standby mode.

In a third aspect, in addition to or in place of other aspects herein, the method can further include reassessing the SNR of the selected spatially unique measurement vector at a predetermined time interval to determine if a spatially unique measurement vector having an optical emitter in the standby mode exhibits a SNR that is greater than the selected spatially unique measurement vector; and switching from the selected spatially unique measurement vector to one of the non-selected spatially unique measurement vectors if it is determined that the non-selected spatially unique measurement vector reports a higher SNR than the selected spatially unique measurement vector.

In a fourth aspect, in addition to or in place of other aspects herein, the method can further include assessing the SNR for the selected spatially unique measurement vector at a plurality of gain values for the TIA to determine a gain value exhibiting a highest SNR.

In a fifth aspect, in addition to or in place of other aspects herein, the method can further include varying the current provided to the optical emitters, wherein selecting the spatially unique measurement vector having the highest SNR comprises selecting the spatially unique measurement vector having the highest SNR at the lowest current for the optical emitters.

In a sixth aspect, in addition to or in place of other aspects herein, the plurality of spatially unique measurement vectors can include a set of short vectors and a set of long vectors; the long vectors having a distance between associated optical emitter and optical detector that is greater than a distance between associated optical emitters and optical detectors for the short vectors.

In a seventh aspect, in addition to or in place of other aspects herein, selecting the spatially unique measurement vector having the highest SNR can include selecting at least one short vector and at least one long vector.

In an eighth aspect, in addition to or in place of other aspects herein, the plurality of spatially unique measurement vectors can be arrayed radially around a central optical detector.

In a ninth aspect, in addition to or in place of other aspects herein, the plurality of spatially unique measurement vectors can be arrayed substantially parallel to one another.

In a tenth aspect, in addition to or in place of other aspects herein, the plurality of spatially unique measurement vectors can be arrayed circumferentially around an outer surface of a cylindrical structure.

In an eleventh aspect, in addition to or in place of other aspects herein, assessing the SNR for each spatially unique measurement vector can include subtracting the portion of the signal from the optical detector caused by ambient light.

In a twelfth aspect, in addition to or in place of other aspects herein, a method for determining an optimal spatial vector in a reflective optical medical sensor device is included. The method can include placing a reflective optical medical sensor device on or in a patient. The reflective optical medical sensor device can include one or more optical emitters; one or more optical detectors; and a measurement circuit having one or more transimpedance amplifiers (TIA). Unique pairs of the optical emitters and the optical detectors can define a plurality of spatially unique measurement vectors. The method can include setting the TIA to a fixed gain value and then turning on the optical emitter associated with each spatially unique measurement vector and receiving reflected light with the associated optical detector for each spatially unique measurement vector at the same fixed gain value. The method can include assessing the SNR for each spatially unique measurement vector. The method can include selecting spatially unique measurement vectors having SNRs above a threshold value. If more than one spatially unique measurement vector exhibits a SNR above the threshold value, then the method can include assessing the SNR for each selected spatially unique measurement vector at a plurality of gain values for the TIA and selecting a single spatially unique measurement vector and single gain value having the highest SNR at the lowest current. The method can include conducting ongoing assessment of the patient by causing the optical emitter associated with the selected single spatially unique measurement vector to emit light and receiving reflected light therefrom with the optical detector associated with the selected spatially unique measurement vector.

In a thirteenth aspect, in addition to or in place of other aspects herein, if no spatially unique vector exhibits a SNR above the threshold value, then the method can include increasing the current provided to the one or more optical emitters and then again assessing the SNR for each spatially unique measurement vector.

In a fourteenth aspect, in addition to or in place of other aspects herein, if no spatially unique vector exhibits a SNR above the threshold value, then the method can include increasing the current provided to the one or more optical emitters, reducing the gain of the TIA, and then again assessing the SNR for each spatially unique measurement vector.

In a fifteenth aspect, in addition to or in place of other aspects herein, the method can further include putting all optical emitters associated with non-selected spatially unique measurement vectors in a standby mode.

In a sixteenth aspect, in addition to or in place of other aspects herein, the method can further include reassessing the SNR of the selected spatially unique measurement vector at a given time interval to determine if a spatially unique measurement vector having an optical emitter in the standby mode exhibits a SNR that is greater than the selected spatially unique measurement vector; and switching from the selected spatially unique measurement vector to one of the non-selected spatially unique measurement vectors if it is determined that the non-selected spatially unique measurement vector reports a higher SNR than the selected spatially unique measurement vector.

In a seventeenth aspect, in addition to or in place of other aspects herein, the method can further include assessing the SNR for the selected spatially unique measurement vector at a plurality of gain values for the TIA to determine a gain value exhibiting a highest SNR.

In an eighteenth aspect, in addition to or in place of other aspects herein, the method can further include varying the current provided to the optical emitters, wherein selecting the spatially unique measurement vector having the highest SNR comprises selecting the spatially unique measurement vector having the highest SNR at the lowest current for the optical emitters.

In a nineteenth aspect, in addition to or in place of other aspects herein, the spatially unique measurement vectors can include a set of short vectors and a set of long vectors; the long vectors having a distance between associated optical emitter and optical detector that is greater than a distance between associated optical emitters and optical detectors for the short vectors.

In a twentieth aspect, in addition to or in place of other aspects herein, a reflective optical medical sensor device is included. The reflective optical medical sensor device can include one or more optical emitters and one or more optical detectors. Unique pairs of the optical emitters and the optical detectors can define a plurality of spatially unique measurement vectors. The reflective optical medical sensor device can include a measurement circuit having one or more transimpedance amplifiers (TIA). The measurement circuit can be configured to set the TIA to a fixed gain value and then turn on the optical emitter associated with each spatially unique measurement vector and receive reflected light with the associated optical detector for each spatially unique measurement vector at the same fixed gain value. The measurement circuit can be configured to assess the signal-to-noise (SNR) for each spatially unique measurement vector. The measurement circuit can be configured to select the spatially unique measurement vector having the highest SNR. The measurement circuit can be configured to conduct ongoing monitoring of the patient by causing the optical emitter associated with the selected spatially unique measurement vector to emit light and receive reflected light therefrom with the optical detector associated with the selected spatially unique measurement vector.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Reflective optical sensors can be extremely useful for gathering information about a patient. Such sensors can be disposed on the patient's skin (such as on the chest, on an arm, leg, neck or the like) or inside of the patient (such as disposed on an endoscopy device or an implanted device). Some reflective sensors herein can include one or more optical emitters, one or more optical detectors, and a measurement circuit having one or more transimpedance amplifiers (TIA). Unique pairs of the optical emitters and the optical detectors can define a plurality of spatially unique measurement vectors.

Having multiple measurement options can be important when trying to manage perfusion heterogeneity within an individual and within a population. Perfusion is the process by which the heart delivers blood to the capillary beds during the cardiac cycle. Low perfusion—when there is a decrease in blood flow to and from the capillaries—is a common phenomenon in individuals with heart conditions, diabetes, obesity, arterial disorders, circulation problems, and the like. Low perfusion is also common in elderly populations and during exposure to cold environments.

Low perfusion can cause a low signal-to-noise ratio (SNR) and thus interfere with accurate detection of physiological parameters. To optimize signal detection, an array of spatially unique measurement vectors taking measurements over a different and/or larger surface area can help mitigate the low perfusion, and thus result in a low SNR. However, the demand on the battery life can be very high if all optical emission and detection channels are utilized at the same time.

One way to preserve battery power and to keep costs and resources to a minimum, is to configure the reflective optical medical sensors described herein to undergo an indexing step to choose a spatially unique measurement vector for use during measurements of a physiological parameter.

There is clinical value in being able to choose a particular spatially unique measurement vector for use quickly. However, full evaluation of reflective optical sensors can be significantly time consuming as a calibration procedure could include assessing the SNR at a plurality of current levels for the optical emitters and at a plurality of gain values for transimpedance amplifiers connected to the optical detectors.

Embodiments herein allow for the rapid calibration of a reflective optical medical sensor device. In some embodiments, a method for rapidly determining an optimal spatial vector for a reflective optical medical sensor device is included. The method can include placing a reflective optical medical sensor device on or in a patient. The reflective optical medical sensor device can include one or more optical emitters, one or more optical detectors and a measurement circuit including one or more transimpedance amplifiers (TIA). In some embodiments, the measurement circuit can include a conversion device, such as an analog front-end controller. Unique pairs of the optical emitters and the optical detectors define a plurality of spatially unique measurement vectors.

The method can further include setting the TIA to a fixed gain value and then turning on the optical emitter associated with each spatially unique measurement vector and receiving reflected light with the associated optical detector for each spatially unique measurement vector at the same fixed gain value. The method can further include assessing the SNR for each spatially unique measurement vector and selecting the spatially unique measurement vector or vectors having the highest SNR. The method can further include conducting ongoing monitoring of the patient by causing the optical emitter associated with the selected spatially unique measurement vector or vectors to emit light and receiving reflected light therefrom with the optical detector associated with the selected spatially unique measurement vector or vectors.

Figure 1:
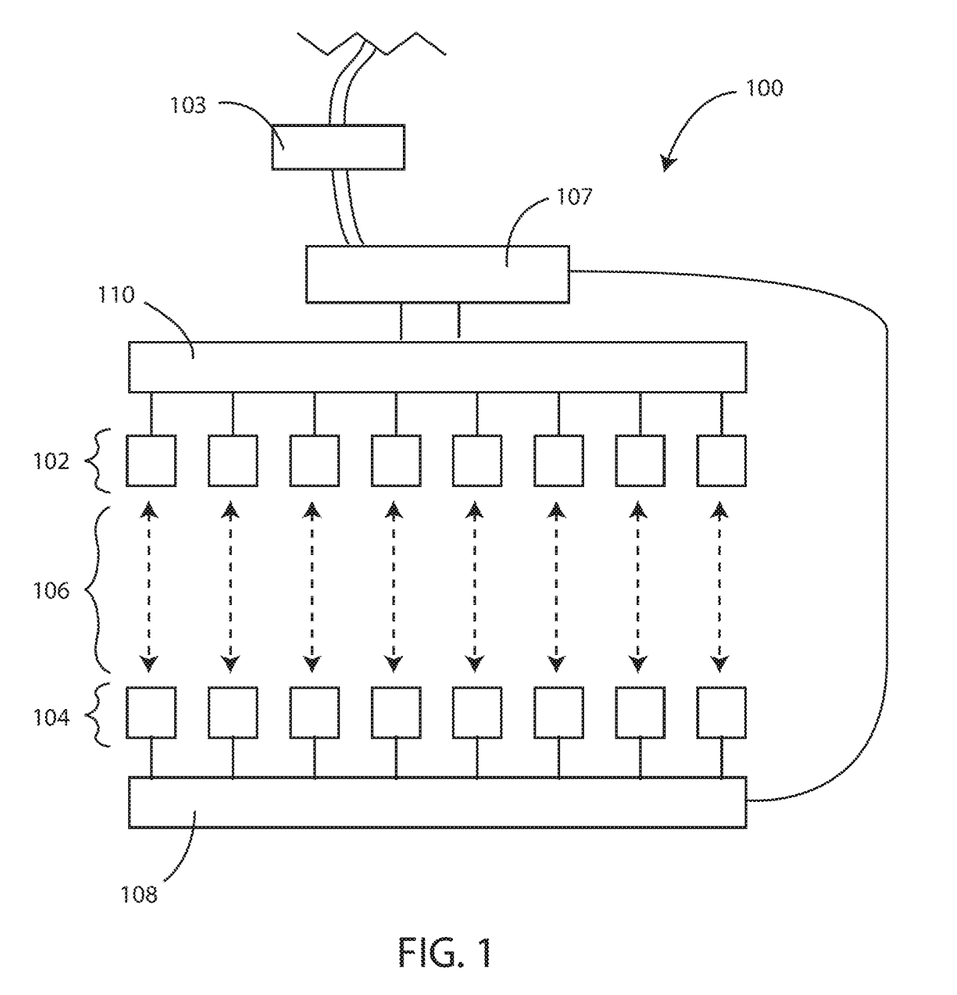
FIG. 1 is a schematic diagram of a portion of a reflective optical medical sensor device in accordance with various embodiments herein.

Referring now to FIG. 1 a schematic diagram of a portion of a reflective optical medical sensor device 100 is shown in accordance with various embodiments herein. The device 100 can include a plurality of optical emitters 102 and a plurality of optical detectors 104. Unique pairs of the optical emitters 102 and the optical detectors 104 define a plurality of spatially unique measurement vectors 106. In some embodiments, the operation of the optical emitters 102 can be controlled by a measurement circuit 107. In some embodiments, the operation of the optical emitters 102 can be controlled by a controller 103. In some embodiments, the operation of the optical emitters 102 can be controlled by a measurement circuit 107 and a controller 103. The controller 103 can include various components including, but not limited to, a microprocessor, a microcontroller, an application specific integrated circuit (ASIC), memory, one or more buses, input and/or output channel interfaces; and the like. The controller can be in electrical communication with measurement circuit 107. In some embodiments, the controller 103 can be integrated into the measurement circuit 107.

In some embodiments, the system can include a multiplexor 110 or manifold to provide selective communication between one or more of the optical emitters 102 and the measurement circuit 107. Further, in some embodiments, the system can include a multiplexor 108 or manifold to provide selective communication between one or more of the optical detectors 104 and the measurement circuit 107.

Figure 2:
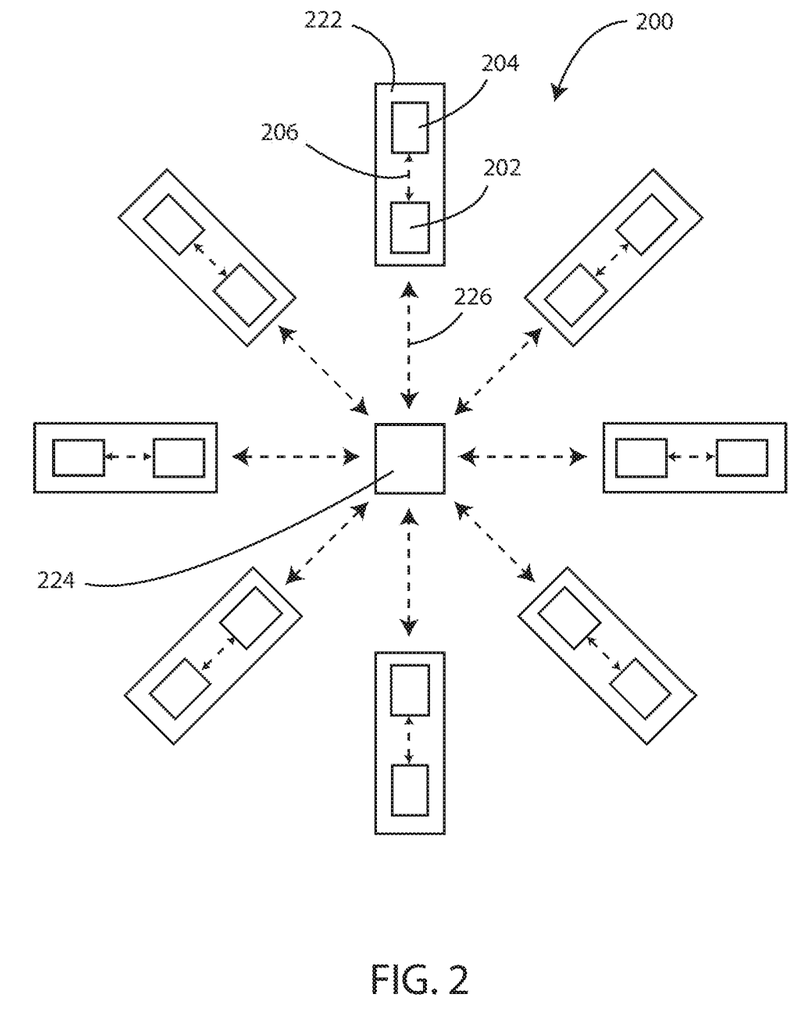
FIG. 2 is a schematic diagram of a portion of a reflective optical medical sensor device in accordance with various embodiments herein.

Many different configurations for reflective optical medical sensor devices are contemplated herein. Referring now to FIG. 2 a schematic diagram of a portion of a reflective optical medical sensor device 200 is shown in accordance with various embodiments herein. In this embodiment, a plurality of spatially unique measurement vectors are arrayed radially around a central optical detector 224. In this embodiment, the spatially unique measurement vectors including a set of short vectors 206 (between optical emitters 202 and optical detectors 204) and including a set of long vectors 226 (between optical emitters 202 and the central optical detector 224). In some embodiments, unique pairs of optical emitters 202 and optical detectors 204 can be disposed together on integrated units 222. However, in other embodiments, the optical emitters 202 and optical detectors 204 can be entirely physically separate from one another.

In the embodiment shown in FIG. 2, the plurality of spatially unique measurement vectors are radially distributed about a central optical detector 224. In some embodiments, the unique measurement vectors are radially spaced 45 degrees apart about a central optical detector in about the same location as the unique pairs. In some embodiments, the spatially unique measurement vectors are radially spaced about 33, 36, 40, 45, 51, 60, 72, or 90 degrees apart about a central optical detector in the same location as the unique pairs.

In some embodiments, the plurality of spatially unique measurement vectors can be arranged in a substantially planar manner, such as with a plurality of spatially unique measurement vectors on a surface of a substantially flat pad. In some embodiments, the plurality of spatially unique measurement vectors can be arrayed substantially parallel to one another. In other embodiments, the arrangement of the plurality of spatially unique measurement vectors may take on a three-dimensional aspect, such as being arranged circumferentially around a cylindrical structure such as a catheter or a scope, such as an endoscopy device. In some embodiments, the plurality of spatially unique measurement vectors can be oriented parallel to a lengthwise axis of a catheter or scope. In some embodiments, the cylindrical structure can include a balloon catheter having the plurality of spatially unique measurement vectors disposed radially about the circumference of the balloon in the collapsed position. In some embodiments, the balloon catheter can be expandable.

Figure 3:
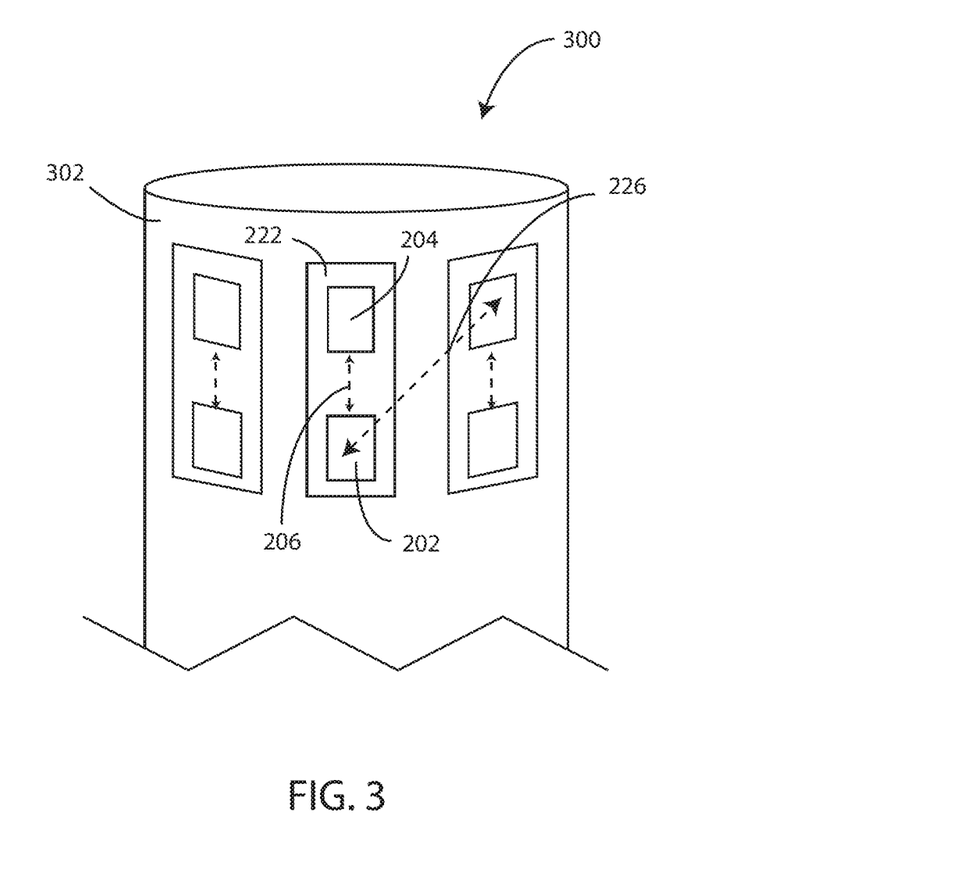
FIG. 3 is a schematic diagram of a portion of a reflective optical medical sensor device in accordance with various embodiments herein.

Referring now to FIG. 3 a schematic diagram is shown of a portion of a reflective optical medical sensor device 300 in accordance with various embodiments herein. The reflective optical medical sensor device 300 can include a plurality of spatially unique measurement vectors disposed within an integrated unit 222 or between integrated units 222. In some embodiments, the short vectors 206 can be arrayed circumferentially around an outer surface of a central cylindrical structure 302. In some embodiments, the short vectors 206 can be arrayed circumferentially around an outer surface of a central cylindrical structure 302 about 90 degrees apart. In some embodiments, the short vectors 206 can be arrayed circumferentially around an outer surface of a central cylindrical structure 302 about 45 degrees apart. In yet other embodiments, the short vectors 206 can be arrayed circumferentially around an outer surface of a central cylindrical structure 302 at least about 30, 60, 120, or 180 degrees apart.

In some embodiments, such as that shown in FIG. 3, the short vectors 206 can be formed within pairs of optical emitters 202 and optical detectors 204 in the same plane about the central cylindrical structure 302. Additionally, the long vectors 226 can be formed between optical emitters 202 and optical detectors 204 found in neighboring planes distributed about the central cylindrical structure 302. In some embodiments, pairs of optical emitters 202 and optical detectors 204 can be disposed together on integrated units 222. Yet in other embodiments, the optical emitters 202 and optical detectors 204 can be entirely physically separate from one another.

It will be appreciated that the plurality of spatially unique measurement vectors can include set of short vectors and a set of long vectors. Each long vector can have a distance between an associated optical emitter and optical detector pair that is greater than the distance between an associated optical emitter and optical detector pair for each short vector.

Rapid Calibration Methods

Figure 4:
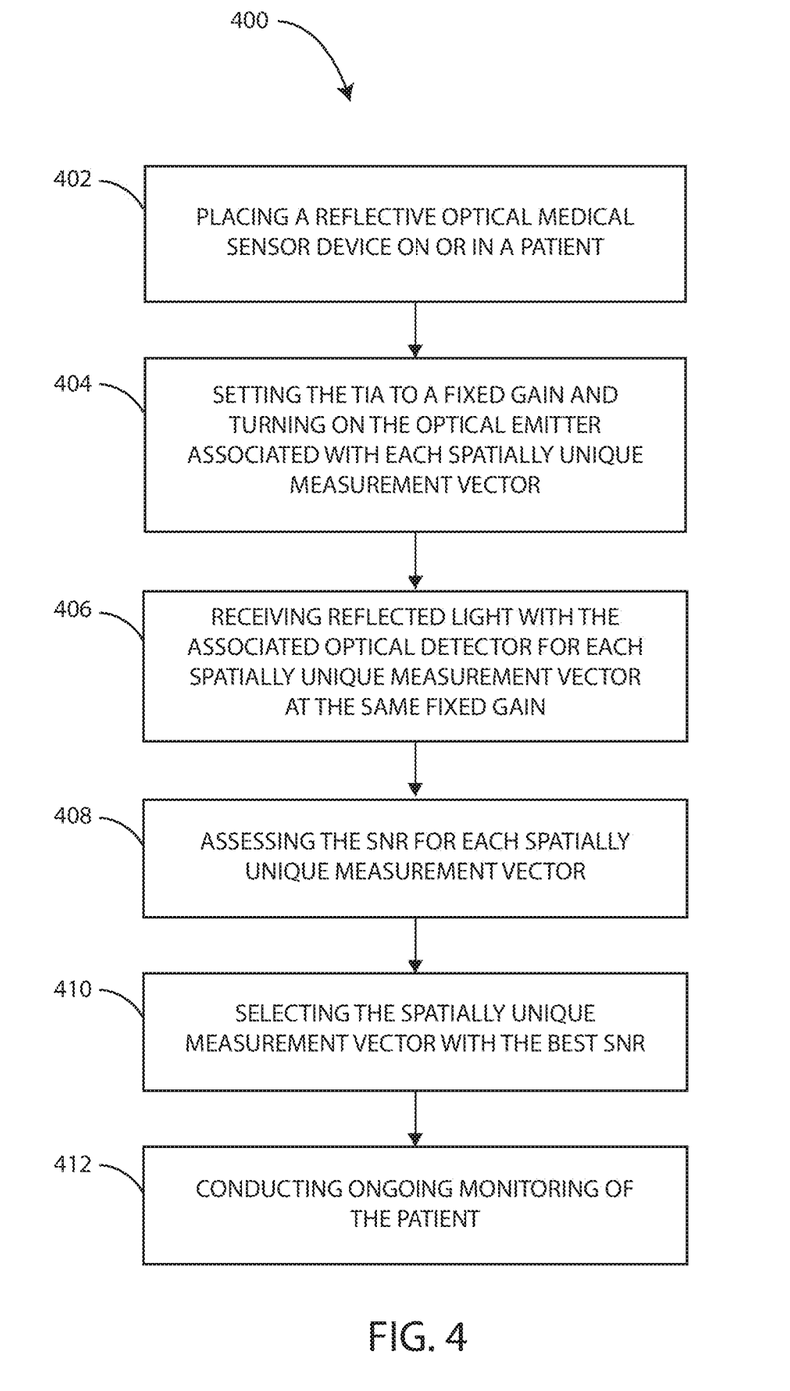
FIG. 4 is a schematic flow diagram of a method of determining an optimal spatial vector for a reflective optical medical sensor device in accordance with various embodiments herein.

Embodiments herein can include various methods. Exemplary methods can include any of the approaches and/or operations described herein. In an embodiment, a method for rapidly determining an optimal spatial vector or vectors for a reflective optical medical sensor device is included. Referring now to FIG. 4, a method 400 can include placing a reflective optical medical sensor device on or in a patient at 402. The reflective optical medical sensor device can include one or more optical emitters, one or more optical detectors and a measurement circuit having one or more transimpedance amplifiers (TIA). In some embodiments, the measurement circuit can include a conversion device. In some embodiments, the measurement circuit can include a conversion device, such as an analog front-end controller or the like. Unique pairs of optical emitters and optical detectors can define a plurality of spatially unique measurement vectors. In some embodiments, the unique pairs of optical emitters and optical detectors can include from 4 to 20 spatially unique measurement vectors. In yet other embodiments, the unique pairs of optical emitters and optical detectors can include from 2 to 40 spatially unique measurement vectors.

The method can further include setting the TIA to a fixed gain value at 404 and then turning on the optical emitter associated with each spatially unique measurement vector and receiving reflected light at 406 with the associated optical detector for each spatially unique measurement vector at the same fixed gain value. The method can further include assessing the signal-to-noise ratio (SNR) for each spatially unique measurement vector at 408. The method can further include selecting the spatially unique measurement vector having the highest SNR at 410. The method can further include conducting ongoing monitoring of the patient by causing the optical emitter associated with the selected spatially unique measurement vector to emit light and receiving reflected light therefrom with the optical detector associated with the selected spatially unique measurement vector at 412.

In some embodiments, values regarding raw data and/or calculated data such as SNR can be saved in memory or a register. Raw data and/or calculated data for selected and/or non-selected measurement vectors can be saved.

In some embodiments, the method can further include the step of putting all optical emitters associated with non-selected spatially unique measurement vectors in a standby mode. Standby mode can be a mode where little or no power is delivered to non-selected optical emitters and non-selected optical detectors. As such, standby mode can serve to conserve energy associated with operation of the device or system.

In some embodiments, the method can further include the step of reassessing the SNR of the selected spatially unique measurement vector at a predetermined time interval. For example, at some time interval such as every 2, 5, 10, 15, 20, 30, 45, 60, 90 or more minutes, the method can include determining if a spatially unique measurement vector having an optical emitter in the standby mode (e.g., a non-selected measurement vector) exhibits a SNR that is greater than the selected spatially unique measurement vector and switching from the selected spatially unique measurement vector to one of the non-selected spatially unique measurement vectors if it is determined that the non-selected spatially unique measurement vector reports a higher SNR than the selected spatially unique measurement vector.

In some embodiments, the method can further include the step of assessing the SNR for the selected spatially unique measurement vector at a plurality of gain values for the TIA to determine a gain value exhibiting a highest SNR. In some embodiments, the method can further include the step of assessing the SNR for the selected spatially unique measurement vector at a plurality of gain values for the TIA, while maintaining a constant current, to determine a gain value exhibiting a highest SNR at constant current.

In some embodiments, the method can further include the step of varying the current provided to the optical emitters, wherein selecting the spatially unique measurement vector having the highest SNR comprises selecting the spatially unique measurement vector having the highest SNR at the lowest current for the optical emitters. For example, current provided to the optical emitters can be reduced and the SNR can be assessed for multiple spatially unique measurement vectors and the one with the highest SNR at that reduced current can be selected. In some embodiments, the TIA gain can be fixed while varying the current provided to the optical emitters, and selecting the spatially unique measurement vector having the highest SNR can include selecting the spatially unique measurement vector having the highest SNR at a fixed TIA gain and lowest current for the optical emitters.

As described above, in some embodiments the unique measurement vector can include both long vectors and short vectors. In some embodiments, selecting the spatially unique measurement vector having the highest SNR includes selecting at least one short vector and at least one long vector. It will be appreciated that long vectors can require more current than short vectors due to the longer distances required for a long vector to propagate through tissue from the optical emitters to the optical detectors. In some embodiments, if the absolute distances are known for various spatially diverse measurement vectors, such as for example, 5 mm for short vectors and 10 mm for long vectors, then the current for the long vectors can be set to be between 1.5 to 2 times the amount of current supplied to the short vectors.

In some embodiments, assessing the SNR for each spatially unique measurement vector includes subtracting the portion of the signal from the optical detector caused by ambient light. The portion of the signal provided by ambient light can be assessed by turning off the one or more optical emitters and measuring the light incident on the one or more optical detectors. This portion of the signal can then be subtracted or otherwise subtracted or removed from the signal obtained by the optical detector.

Figure 5:
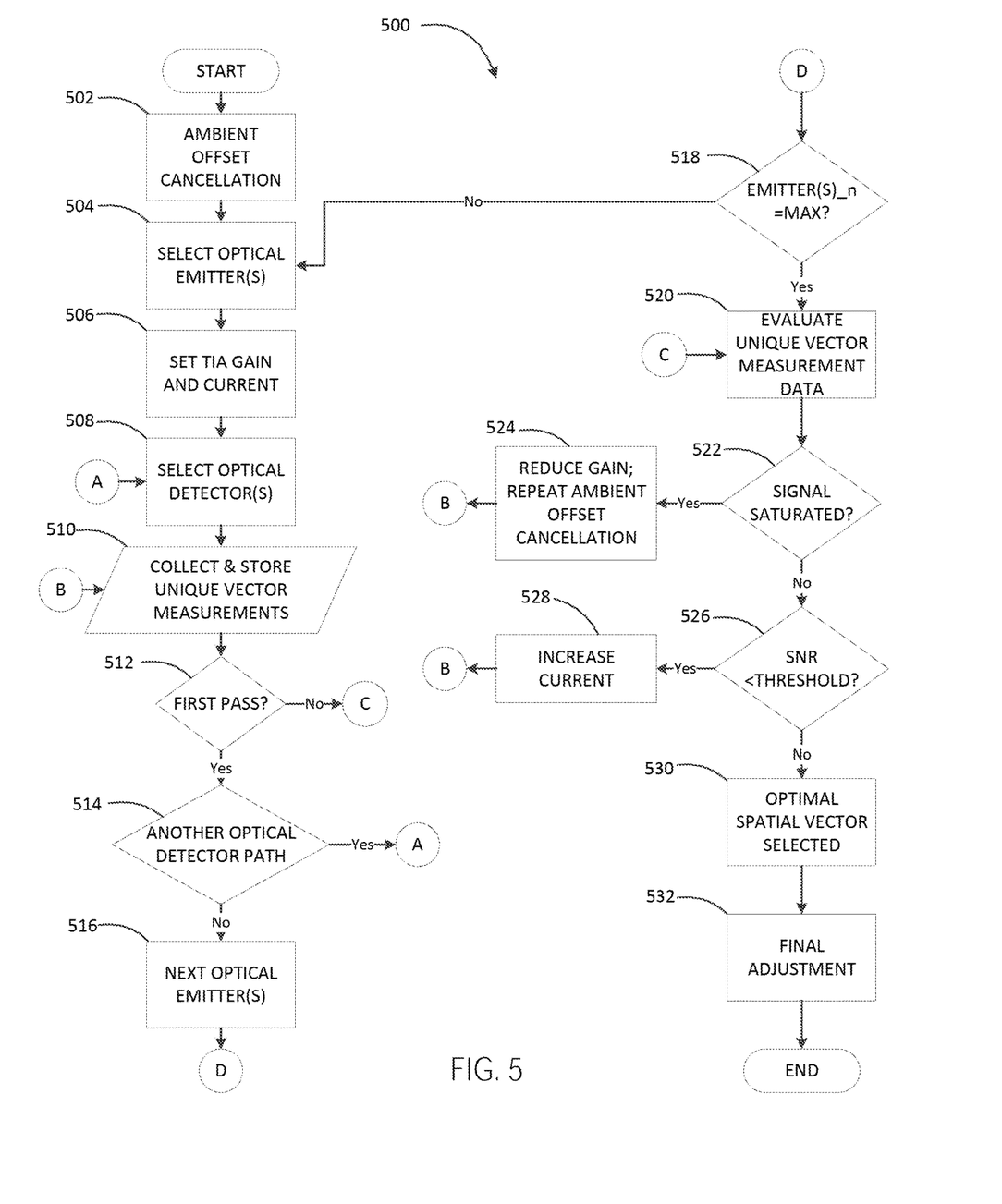
FIG. 5 is a schematic flow diagram of a method of determining an optimal spatial vector for a reflective optical medical sensor device in accordance with various embodiments herein.

Referring now to FIG. 5, a flow chart for an exemplary method 500 to rapidly determine optimal spatial vectors is shown in accordance with the embodiments herein. Method 500 starts with an ambient offset cancellation at 502 for each spatially unique measurement vector in an array. It will be appreciated that the physiological signals to be measured by the devices and methods herein can be pulsatile. In contrast, the ambient noise signal present in the environment surrounding the devices can be relatively constant. In some embodiments, the ambient offset cancellation can include taking a measurement at each optical detector for each spatially unique measurement vector when the optical emitters are turned off, and recording the values into memory. The same measurements can be taken for each spatially unique measurement vector using a fixed TIA gain and given current, and recorded into memory. The signal recorded when no current is supplied to the optical emitters (i.e., the ambient component or the background signal) can be subtracted from the signal recorded using a fixed TIA gain and given current to yield a background-corrected signal. However, various other approaches to mitigating the effects of background noise are also contemplated herein.

It will be appreciated that in some embodiments, a starting point for the ambient offset cancellation 502 can include setting the TIA gain to the lowest allowable value while setting the current supplied to the optical emitters at the highest allowable value prior to beginning the ambient offset cancellation step. In yet other embodiments, a starting point for the ambient offset cancellation 502 can include setting the TIA gain to the highest allowable value while setting the current supplied to the optical emitters at the lowest allowable value prior to beginning the ambient offset cancellation step. In some embodiments, any time the gain of the TIA is changed, a new ambient offset cancellation step can be performed.

The ambient offset cancellation at 502 can include setting the gain of the TIA to a fixed value. With the TIA gain fixed, each unique pair of optical emitters and optical detectors associated with each spatially unique measurement vector can be individually interrogated. Each optical emitter can be turned on sequentially and the reflected light can be received at the paired optical detector for each spatially unique measurement vector. The received light signal can be recorded by the measurement circuit. In some embodiments, the TIA fixed gain is set to a value of at least ⅓ the full dynamic range of the measurement circuit associated with the reflective optical sensor device. In some embodiments, the TIA fixed gain is set to a value of at least ¼ the full dynamic range of the measurement circuit associated with the reflective optical sensor device. In other embodiments, the TIA fixed gain is set to a value of at least ½ the full dynamic range of the measurement circuit associated with the reflective optical sensor device. Suitable measurement circuits including a measurement circuit having one or more TIA components associated therewith are described more fully below.

One or more optical emitters for each group of short vectors and each group of long vectors within the spatially unique measurement vectors can be selected on at least a first pass through the method by evaluating the highest SNR for a fixed TIA gain at a given current. The current supplied to each optical emitter during the ambient offset cancellation at 502 can be attenuated to provide the highest SNR without saturating the optical detectors. Optimal currents can be selected from those described below with respect to step 506. The one or more optical emitters for the group of short vectors and group of long vectors can be selected at 504 for further tuning based on those that utilize the lowest current and display the highest SNR recorded by the optical detectors.

The TIA gain and the current supplied to the optical emitter(s) can be set at 506 following the selection of the optical emitter(s) at 504. In particular, as described with respect to ambient offset cancellation, the TIA gain can be fixed to a value of at least ⅓ the full dynamic range of the measurement circuit associated with the reflective optical sensor device. In some embodiments, the TIA fixed gain can be set to a value of at least ¼ the full dynamic range of the measurement circuit associated with the reflective optical sensor device. In other embodiments, the TIA fixed gain can be set to a value of at least ½ the full dynamic range of the measurement circuit associated with the reflective optical sensor device.

Setting the current at 506 can included varying the current provided to the optical emitters at a predetermined fixed TIA gain value. While maintaining a fixed gain on the TIA, the current can be supplied to the optical emitter(s) in a range between about 50-70 mA. In some embodiments, the current supplied to the optical emitters can be 10 mA, 20 mA, 30 mA, 40 mA, 50 mA, 60 mA, 70 mA, 80 mA, 90 mA, 100 mA, 125 mA, 150 mA, 175 mA, and 200 mA. In some embodiments, the amount of current applied to the optical emitters can be in a range between any of the foregoing values, provided the lower range is smaller than the upper range. Further tuning can include optimization of the unique pairs of optical emitters and optical detectors at various combinations of fixed TIA gain and optical emitter current.

The one or more optical detectors for each spatially unique measurement vector can be selected at 508. For example, this can be accomplished by indexing a software controlled switch, such as an inter-integrated circuit (I²C), serial peripheral interface (SPI) or similar device, which can selectively activate each optical emitter and take a reading from each optical detector associated with that optical emitter. As measurements are recorded to obtain an average score for each spatially unique vector measurement, each of the short vectors and long vectors can be evaluated for those having the highest peak and highest SNR for the settings applied in step 506. Following the selection of optical detectors at 508, multiple measurements for the chosen optical emitter and optical detector pairs can be recorded at 510 for further analysis.

If it is determined that the method is on the first pass at 512, then the method proceeds to 514. If it is determined that the method is no longer on the first pass through, then the method proceeds to Point C, as will be discussed below with respect to 520.

At 514, a determination is made as to whether or not there is another optical detector path to be assessed for the selected optical emitter. If yes, then the method returns to Point A to allow for selection of another optical detector. If no, then the method proceeds 516, where the next group of optical emitters to be tuned can be analyzed at Point D. At Point D, the method moves to 518 where a determination is made as to whether or not the maximum number of optical emitters in the group of optical emitters has been tuned. The maximum number of optical emitters to be tuned can be determined by the maximum number of optical emitters present in the optical medical sensor device. In some embodiments, the maximum number of optical emitters can be any predetermined number of optical emitters present in the optical medical sensor device, as long as at least one optical emitter is present. In some embodiments, the number of optical emitters present in the optical medical sensor device can be between 4 and 40.

If it is determined that the maximum number of optical emitters has not been tuned, the method goes back to 504 the selection of the optical emitter(s). If it is determined that the maximum number of optical emitters has been tuned, then the method moves on to 520, and an evaluation of the data recorded at 510 begins. The evaluation can include determining the highest peak associated within the selected group of optical emitters. Upon selection of the highest peak, the method can make a determination as to whether or not the detected signal is saturated at 522. If the signal is saturated, the TIA gain can be lowered for the selected group of one or more optical emitters and a new ambient offset cancellation procedure can be performed at 524. The method can then move back to Point B. If the signal is not saturated at 522, then the method can move on to 526 where the SNR is analyzed.

The SNR can be assessed for the selected peak signal or for signals corresponding to each spatially unique measurement vector. In some embodiments, the assessment can include selecting one or more spatially unique measurement vectors having SNR above a threshold value. Threshold values can vary. In some embodiments the threshold value is at or above about 60 dB. In some embodiments, the threshold value can be at or above about 40 dB, 45 dB, 50 dB, 55 dB, 60 dB, 65 dB, 70 dB, 75 dB, 80 dB, 85 dB, 90 dB, or 95 dB, or a value falling within a range, wherein any of the foregoing can serve as the upper or lower bound of the range, provided that the upper bound is greater than the lower bound.

If the SNR value(s) are less than a threshold value (e.g., no spatially unique measurement vectors exhibit a SNR above the threshold value), then the method can include increasing the current provided to the one or more optical emitters at 528. In some embodiments, if no spatially unique measurement vector exhibits a SNR ratio above the threshold value, then the method can include increasing the current provided to the one or more optical emitters and reducing the gain of the TIA at 528. If the current is increased, with or without a reduction in the gain, the method returns to Point B.

In various embodiments, if no spatially unique vector exhibits a SNR above the threshold value, then the method can include increasing the current provided to the one or more optical emitters and then again assessing the SNR for each spatially unique measurement vector.

In various embodiments, if no spatially unique vector exhibits a SNR above the threshold value, then the method can include increasing the current provided to the one or more optical emitters, reducing the gain of the TIA, and then again assessing the SNR for each spatially unique measurement vector.

If one or more spatially unique measurement vectors exhibits a SNR above the threshold value, then the spatially unique measurement vectors having the highest SNR (i.e., an optimal spatial vector) can be selected at 530 and a final TIA gain adjustment at a the given current can be made, if necessary, for the selected optimal spatial vector at 532 to complete the method. Once the method has ended, the reflective optical medical sensor device can be used to monitor a patient.

In various embodiments, if more than one spatially unique measurement vector exhibits a SNR above the threshold value, then the method can further include assessing the SNR for each selected spatially unique measurement vector at a plurality of gain values for the TIA and selecting a single spatially unique measurement vector and single gain value having the highest SNR at the lowest current.

The method can further include assessing the SNR for each selected spatially unique measurement vector at a plurality of gain values for the TIA and selecting a single spatially unique measurement vector and single TIA gain value having the highest SNR at the lowest current.

The method can include selecting the spatially unique measurement vector having the highest SNR and conducting ongoing monitoring of the patient. For example, this can include causing the optical emitter associated with the selected spatially unique measurement vector to emit light and the optical detector associated with the selected spatially unique measurement vector to receive reflected light therefrom with the optical detector associated with the selected spatially unique measurement vector.

Measurement Circuits

Figure 6:
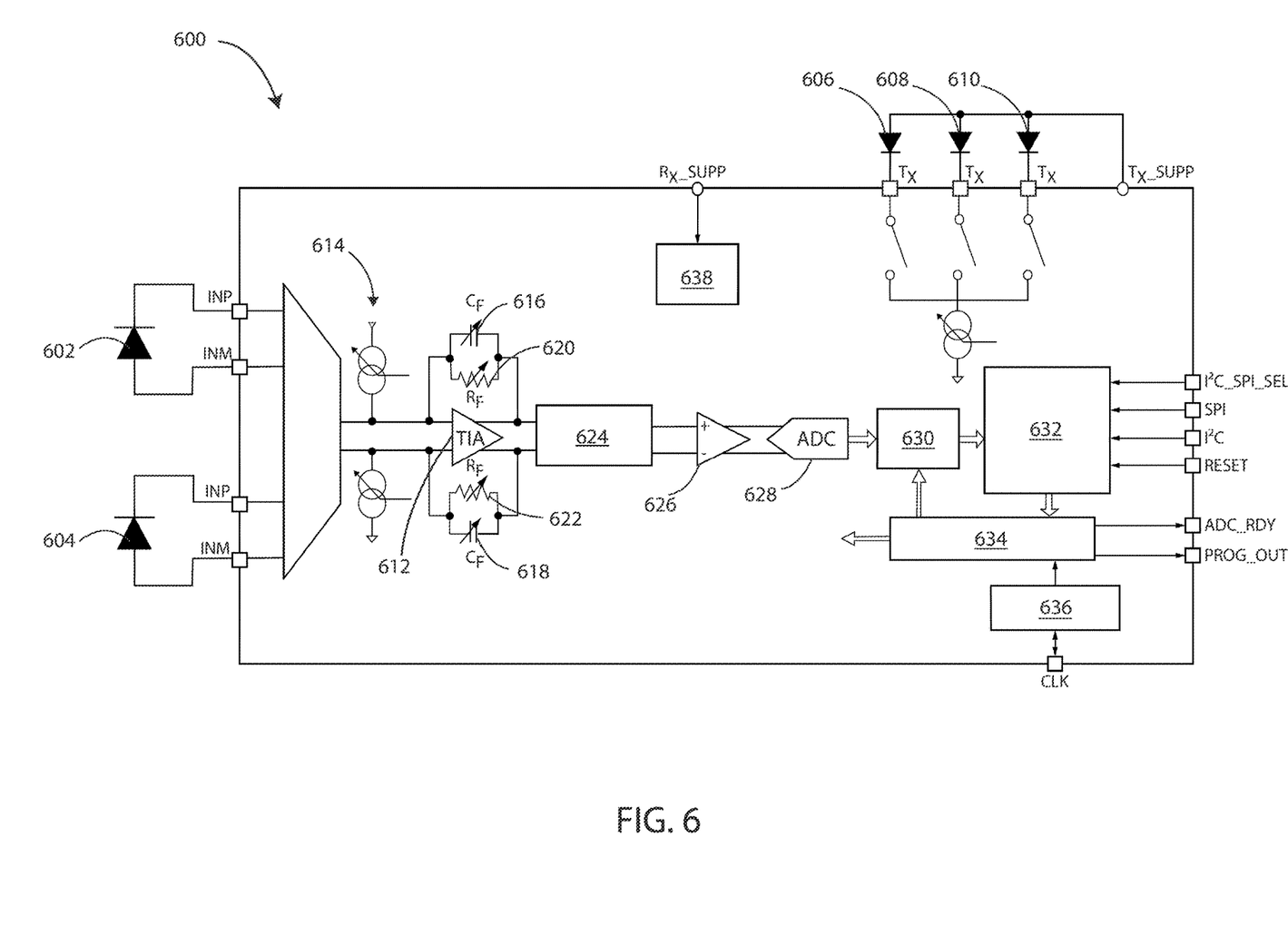
FIG. 6 is a schematic circuit diagram of a measurement circuit in accordance with various embodiments herein.

Various types of measurement circuits can be used in order to control the operation of components described herein, including but not limited to optical emitters, optical detectors, amplifiers (including, but not limited to transimpedance amplifiers), digital-to-analog conversion devices, I²C and SPI interfaces, and the like. Referring now to FIG. 6, a schematic circuit diagram of a measurement circuit 600 is shown in accordance with various embodiments herein.

Measurement circuit 600 can include one or more optical detectors, such as photodiode 602 and photodiode 604, and one or more optical emitters, such as light-emitting diode (LED) 606, LED 608, and LED 610. The measurement circuit 600 shows two optical detectors, however, it will be appreciated that any number of optical detectors between about 2 to 40 can be contemplated herein. Likewise, measurement circuit shows three optical emitters, however, it will be appreciate that any number of optical emitters between about 2 to 40 can be contemplated herein. Measurement circuit 600 can further include one or more transimpedance amplifiers (TIA) 612. Each TIA can be electrically coupled to one or more feedback capacitors ($C_F$), such as $C_F$ 616 and $C_F$ 618, and one or more feedback resistors ($R_F$), such as $R_F$ 620 and $R_F$ 622. The measurement circuit can further include components such as DAC offset 614; noise-reduction filter 624; amplifier 626; analog-to-digital (ADC) converter 628; first-in-first-out (FIFO) component 630; software controlled switch 632 having interfaces for components such as an inter-integrated circuit (I²C), serial peripheral interface (SPI) or similar; timing engine 634; oscillator 636; low drop out (LDO) regulator 638; and the like.

The operation of the optical emitters and optical detectors can be controlled by a measurement circuit as described. In some embodiments, the operation of the optical emitters can be controlled by a controller, such as an analog front-end controller. In some embodiments, the operation of the optical emitters and optical detectors can be controlled by a measurement circuit and a controller. In some embodiments, the measurement circuit and/or controller can be configured to set the TIA to a fixed gain value and then turn on the optical emitter associated with each spatially unique measurement vector and receive reflected light with the associated optical detector for each spatially unique measurement vector at the same fixed gain value. In some embodiments, the measurement circuit and/or controller can be configured to assess the signal-to-noise (SNR) for each spatially unique measurement vector. In some embodiments, the measurement circuit and/or controller can be configured to select the spatially unique measurement vector having the highest SNR. In some embodiments, the measurement circuit and/or controller can be configured to conduct ongoing monitoring of the patient by causing the optical emitter associated with the selected spatially unique measurement vector to emit light and receive reflected light therefrom with the optical detector associated with the selected spatially unique measurement vector.

It will be appreciated that the components shown in FIG. 6 are not meant to be limiting, and that measurement circuit 600 can contain additional components not shown. It will also be appreciated that measurement circuit 600 can contain fewer components than those shown.

Photoplethysmogram Oximetry

Reflective optical medical sensor devices described herein can be used for example when performing reflective photoplethysmogram (PPG) oximetry. PPG oximetry is a minimally invasive technique that can be used to measure blood oxygen saturation (reported as oxygen saturation, or $SpO_2$), heart rate (in beats per minute, i.e., bpm), pulse arrival time, R-R interval, systolic blood pressure, respiratory rate, perfusion index (the ratio of pulsatile blood flow to non-pulsatile blood flow), and the like. PPG can additionally be used to measure the volume of a vessel or an organ. In some embodiments, PPG oximetry can be performed on the chest. In some embodiments, the PPG oximetry can be performed on the chest, specifically over the sternum. PPG oximetry can also be performed on a number of additional sites on the body, including, but not limited to the wrist, the forehead, and the arm.

Generally PPG oximetry is a technique that involves shining one or more wavelengths of light into the skin of a patient and measures the changes in light absorption due to the changes in blood volume at the measurement site. Different wavelengths of light penetrate the tissues at different depths at the measurement site, and thus provide opportunities to measure different physiological parameters. Blood volume at the measurement site can be monitored throughout the cardiac cycle. As the heart contracts during systole, blood is ejected from the left ventricle and is circulated through the arteries. As the heart relaxes during diastole, blood is pulled from the peripheral arteries, through the veins, and drawn back to the heart. Thus, as blood is ejected out of the heart, more blood will flow through the arteries than when the heart relaxes and draws blood back to the heart.

The changes in light absorption due to the changes in blood volume in the arteries and/or arterioles at the measurement site can be determined by illuminating the arteries beneath the surface of the skin with one or more wavelengths of light at various times throughout the cardiac cycle. Different photodiodes having different wavelengths of peak emission can be chosen depending on the physiological parameter to be tested. Analysis can be performed using the data collected from the light absorbed, the light reflected, and the light scattered during illumination to determine one or more of the physiological parameters listed above.

In one example, blood oxygen saturation ($SpO_2$) can be determined by dual-wavelength illumination of the arteries and/or arterioles in the subcutaneous tissue. During each cardiac cycle, as blood is pumped by the heart into the periphery the pulse pressure provides enough force to enlarge the arteries and/or arterioles. Hemoglobin in the blood can absorb light of various wavelengths. To measure $SpO_2$, a PPG device can be used to shine light having wavelengths at or about 660 nm and 950 nm on a specific location, such as the chest or wrist. Absorption of light at that location can be influenced by the level of oxygen saturation of the hemoglobin in the blood in close proximity to the detector(s). Hemoglobin is an oxygen-carrying metalloprotein found in healthy, circulating red blood cells. Each molecule of hemoglobin can carry up to four molecules of oxygen. In a deoxygenated state, hemoglobin absorbs light at or about a wavelength of 660 nm. In an oxygenated state, hemoglobin absorbs light at or about a wavelength of 950 nm. The difference in the amount of absorbance for each wavelength, can be used to calculate a percentage of $SpO_2$ at any given time. The amount of light absorbed can be determined experimentally by analyzing total reflected light at the optical detector. The reflective optical medical sensors described herein can be configured to use the data collected to calculate the percentage $SpO_2$.

In another example, heart rate can be determined by illumination of the arteries and/or arterioles with green light. During each cardiac cycle, as the blood flowing into and out of the underlying arteries and/or arterioles is illuminated with light having a wavelength at or about 530 nm, absorption of the light by the hemoglobin in the blood changes depending on the volume of blood at the measurement site. As blood flows into the measurement site during a heartbeat, the light absorption is greater than it is when the heart is relaxed and blood flow at the measurement site. The reflective optical medical sensors described herein can be configured to illuminate the site in excess of hundreds of times per second and use the data collected to correlate absorption at a given time period with heart rate.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like. "Circuitry" can include both hardwired circuitry for execution of particular operations as well as processors that are programmed to execute instructions to provide the same functionality.

All publications and patent applications in this specification are indicative of the level of ordinary skill in the art to which this specification pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein. As such, the embodiments described herein are not intended to be exhaustive or to limit the scope to the precise forms disclosed herein. Rather, the embodiments are chosen and described so that others skilled in the art can appreciate and understand the principles and practices.

The invention claimed is:

1. A method for determining an optimal spatial vector for a reflective optical medical sensor device, the method comprising:
   placing a reflective optical medical sensor device on or in a patient, the reflective optical medical sensor device comprising:
      one or more optical emitters;
      one or more optical detectors; and
      a measurement circuit having one or more transimpedance amplifiers (TIA);
   wherein the optical medical sensor device includes at least two pairs of the optical emitters and the optical detectors and wherein different pairs of the optical emitters and the optical detectors define a plurality of spatially different measurement vectors;
   setting the TIA to a fixed gain value and then turning on an optical emitter of the one or more optical emitters associated with each spatially different measurement vector and receiving reflected light with an associated optical detector of the one or more optical detectors for each spatially different measurement vector at the same fixed gain value;
   assessing the signal-to-noise (SNR) for each spatially different measurement vector;
   selecting the spatially different measurement vector having the highest SNR; and
   conducting ongoing monitoring of the patient by causing the optical emitter associated with the selected spatially different measurement vector to emit light and receiving reflected light therefrom with the optical detector associated with the selected spatially different measurement vector.

2. The method of claim 1, further comprising putting all optical emitters associated with non-selected spatially different measurement vectors in a standby mode.

3. The method of claim 2, further comprising reassessing the SNR of the selected spatially different measurement vector at a predetermined time interval to determine if a spatially different measurement vector having an optical emitter in the standby mode exhibits a SNR that is greater than the selected spatially different measurement vector; and
   switching from the selected spatially different measurement vector to one of the non-selected spatially different measurement vectors if it is determined that the non-selected spatially different measurement vector reports a higher SNR than the selected spatially different measurement vector.

4. The method of claim 1, further comprising assessing the SNR for the selected spatially different measurement vector at a plurality of gain values for the TIA to determine a gain value exhibiting a highest SNR.

5. The method of claim 1, further comprising varying the current provided to the optical emitters, wherein selecting the spatially different measurement vector having the highest SNR comprises selecting the spatially different measurement vector having the highest SNR at the lowest current for the optical emitters.

6. The method of claim 1, the plurality of spatially different measurement vectors comprising a set of short vectors and a set of long vectors; the long vectors having a distance between associated optical emitter and optical detector that is greater than a distance between associated optical emitters and optical detectors for the short vectors.

7. The method of claim 1, wherein selecting the spatially different measurement vector having the highest SNR includes selecting at least one short vector and at least one long vector.

8. The method of claim 1, wherein the plurality of spatially different measurement vectors are arrayed radially around a central optical detector.

9. The method of claim 1, wherein the plurality of spatially different measurement vectors are arrayed substantially parallel to one another.

10. The method of claim 1, wherein the plurality of spatially different measurement vectors are arrayed circumferentially around an outer surface of a cylindrical structure.

11. The method of claim 1, wherein assessing the SNR for each spatially different measurement vector includes subtracting the portion of the signal from the optical detector caused by ambient light.

12. A method for determining an optimal spatial vector in a reflective optical medical sensor device, the method comprising:
   placing a reflective optical medical sensor device on or in a patient, the reflective optical medical sensor device comprising:
      one or more optical emitters;
      one or more optical detectors; and
      a measurement circuit having one or more transimpedance amplifiers (TIA); wherein the optical medical sensor device includes at least two pairs of the optical emitters and the optical detectors and wherein different pairs of the optical emitters and the optical detectors define a plurality of spatially different measurement vectors;
   setting the TIA to a fixed gain value and then turning on the optical emitter associated with each spatially different measurement vector and receiving reflected light with the associated optical detector for each spatially different measurement vector at the same fixed gain value;
   assessing the signal-to-noise ratio (SNR) for each spatially different measurement vector;
   selecting spatially different measurement vectors having SNRs above a threshold value; if more than one spatially unique measurement vector exhibits a SNR above the threshold value, then assessing the SNR for each selected spatially different measurement vector at a plurality of gain values for the TIA and selecting a single spatially different measurement vector and single gain value having the highest SNR at the lowest current; and
   conducting ongoing assessment of the patient by causing the optical emitter associated with the selected single spatially different measurement vector to emit light and receiving reflected light therefrom with the optical detector associated with the selected spatially different measurement vector.

13. The method of claim 12, if no spatially different vector exhibits a SNR above the threshold value, then increasing the current provided to the one or more optical emitters and then again assessing the SNR for each spatially different measurement vector.

14. The method of claim 12, if no spatially different vector exhibits a SNR above the threshold value, then increasing the current provided to the one or more optical emitters, reducing the gain of the TIA, and then again assessing the SNR for each spatially different measurement vector.

15. The method of claim 12, further comprising putting all optical emitters associated with non-selected spatially different measurement vectors in a standby mode.

16. The method of claim 12, further comprising reassessing the SNR of the selected spatially different measurement vector at a given time interval to determine if a spatially different measurement vector having an optical emitter in the standby mode exhibits a SNR that is greater than the selected spatially different measurement vector; and
    switching from the selected spatially different measurement vector to one of the non-selected spatially different measurement vectors if it is determined that the non-selected spatially different measurement vector reports a higher SNR than the selected spatially different measurement vector.

17. The method of claim 12, further comprising assessing the SNR for the selected spatially different measurement vector at a plurality of gain values for the TIA to determine a gain value exhibiting a highest SNR.

18. The method of claim 12, further comprising varying the current provided to the optical emitters, wherein selecting the spatially different measurement vector having the highest SNR comprises selecting the spatially different measurement vector having the highest SNR at the lowest current for the optical emitters.

19. The method of claim 12, the plurality of spatially different measurement vectors comprising a set of short vectors and a set of long vectors; the long vectors having a distance between associated optical emitter and optical detector that is greater than a distance between associated optical emitters and optical detectors for the short vectors.

20. A reflective optical medical sensor device comprising:
    one or more optical emitters;
    one or more optical detectors;
    wherein the optical medical sensor device includes at least two pairs of the optical emitters and the optical detectors and wherein combinations of optical emitters and optical detectors form different pairs; wherein the different pairs of the optical emitters and the optical detectors define a plurality of spatially different measurement vectors; and
    a measurement circuit having one or more transimpedance amplifiers (TIA);
    a controller in electrical communication with the measurement circuit, wherein the controller is configured to:
    set the TIA to a fixed gain value and then turn on the optical emitter associated with each spatially different measurement vector and receive reflected light with the associated optical detector for each spatially different measurement vector at the same fixed gain value;
    assess the signal-to-noise (SNR) for each spatially different measurement vector;
    select the spatially different measurement vector having the highest SNR; and
    conduct ongoing monitoring of the patient by causing the optical emitter associated with the selected spatially different measurement vector to emit light and receive reflected light therefrom with the optical detector associated with the selected spatially different measurement vector.

* * * * *